United States Patent [19]

Bordenick

[11] Patent Number: 4,814,058
[45] Date of Patent: Mar. 21, 1989

[54] MEASURING ELECTRODE ASSEMBLY

[75] Inventor: John E. Bordenick, West Mifflin, Pa.

[73] Assignee: The United States of America as represented by the United States Department of Energy, Washington, D.C.

[21] Appl. No.: 186,419

[22] Filed: Apr. 26, 1988

[51] Int. Cl.⁴ ............................................. G01N 27/30
[52] U.S. Cl. ................................... 204/401; 204/420; 204/433; 204/435
[58] Field of Search ............... 204/435, 433, 420, 401, 204/1 H

[56] References Cited

U.S. PATENT DOCUMENTS

| | | | |
|---|---|---|---|
| 3,476,671 | 11/1969 | Petty | 204/195 |
| 3,546,087 | 12/1970 | Friconneau et al. | 204/195 |
| 3,666,651 | 5/1972 | Makabe | 204/195 G |
| 4,008,141 | 2/1977 | Kotani et al. | 204/195 G |
| 4,012,308 | 3/1977 | Jerrold-Jones et al. | 204/195 F |
| 4,128,468 | 12/1978 | Bukamier | 204/195 F |
| 4,182,668 | 1/1980 | Koshiishi et al. | 204/195 L |
| 4,390,406 | 6/1983 | Kato et al. | 204/435 |

Primary Examiner—G. L. Kaplan
Attorney, Agent, or Firm—William W. Randolph; Judson R. Hightower; Richard E. Constant

[57] ABSTRACT

A pH measuring electrode assembly for immersion in a solution includes an enclosed cylindrical member having an aperture at a lower end thereof. An electrolyte is located in the cylindrical member above the level of the aperture and an electrode is disposed in this electrolyte. A ring formed of an ion porous material is mounted relative to the cylindrical member so that a portion of this ring is rotatable relative to and is covering the aperture in the cylindrical member. A suitable mechanism is also provided for indicating which one of a plurality of portions of the ring is covering the aperture and to keep track of which portions of the ring have already been used and become clogged. Preferably, the electrode assembly also includes a glass electrode member in the center thereof including a second electrolyte and electrode disposed therein. The cylindrical member is resiliently mounted relative to the glass electrode member to provide for easy rotation of the cylindrical member relative to the glass electrode member for changing of the portion of the ring covering the aperture.

15 Claims, 1 Drawing Sheet

MEASURING ELECTRODE ASSEMBLY

FIELD OF THE INVENTION

The present invention relates generally to a measuring electrode assembly which is immersed in a solution, and more particularly to a pH measuring combination electrode assembly having a plurality of usable porous member portions selectively moveable into position for use. The Government has rights in this invention pursuant to Contract No. DE-AC11-76PN00014 awarded by the U.S. Department of Energy.

BACKGROUND OF THE INVENTION

Typically, pH combination electrode assemblies utilize a glass frit as a porous member. The function of the glass frit is to separate a silver-silver chloride reference electrode immersed in a potassium chloride solution from the solution under test and yet allow electrical contact to be maintained between the electrode and the solution under test. Unfortunately, the glass frit frequently becomes clogged, for example, by using the electrode assembly to measure the pH of solutions containing particles. More commonly, the glass frit becomes clogged because the silver chloride on the silver-silver chloride electrode is much more soluble in potassium chloride solutions than in the usual solutions under test. As the potassium chloride solution containing dissolved silver chloride slowly flows through the glass frit and meets the solution under test, the dissolved silver chloride precipitates on the surface and/or the interior of the glass frit causing the glass frit to plug and disrupt electrical contact.

When the glass frit becomes plugged, it is possible to return the plug to working condition. For example, the electrode can be immersed in fresh potassium chloride solution which is then heated to near boiling to redissolve the precipitated silver chloride. However, unless one is very careful, this may result in the electrode assembly cracking and rendering it useless. Another method of unplugging the glass frit is to manually pick at the surface to dislodge precipitated silver chloride. However, picking at the surface may also render an electrode useless by destroying the glass frit unless exteme care is taken.

Various electrode assemblies comprising concentric cylindrical tubes and having a porous member providing communication between a solution to be tested and an internal electrolyte are disclosed in the following U.S. Patents: U.S. Pat. No. 3,476,671 (Petty); U.S. Pat. No. 4,390,406 (Kato et al.); U.S. Pat. No. 4,182,668 (Koshiishi et al.); U.S. Pat. No. 3,546,087 (Friconneau et al.); U.S. Pat. No. 4,012,308 (Jerrold-Jones et al.); U.S. Pat. No. 4,008,141 (Kotani et al.); U.S. Pat. No. 3,666,651 (Makabe); and U.S. Pat. No. 4,128,468 (Bukamier).

SUMMARY OF THE INVENTION

In accordance with the present invention, a measuring electrode assembly is provided which is immersed in a solution to be measured. The electrode assembly includes an enclosed member which is preferably cylindrical and which has an aperture at a lower end thereof. An electrolyte is provided in this enclosed member which extends above the level of the aperture. An electrode is also provided in the enclosed member which is immersed in the electrolyte. A porous plug member through which ions are passed is mounted by a mounting means so as to cover the aperture. This porous member allows the eletrolyte ions to slowly flow through the porous member thereby maintaining electrical contact with the solution under test. A plurality of portions of the porous member are selectrvely moveable to cover this aperture when the portion currently in position becomes clogged.

In a preferred embodiment of the present invention, the porous member is in the shape of a ring which is rotatable relative to the aperture. This ring is mounted inside the cylindrical wall of the enclosed member. An indicating means is also preferably provided for indicating which one of the plurality of portions of the porous member is covering the aperture.

According to the preferred embodiment of the present invention, the electrode assembly is a combination electrode assembly including a glass electrode member. The glass electrode member is formed from a tube closed at both ends, a second electrolyte in the tube, and a second electrode in this electrolyte. The tube is disposed concentrically in and in spaced relationship to the enclosed cylindrical member. Upper and lower sealing means are then located about the tube at an upper end and a lower end thereof for sealing an annular space between the tube and the cylindrical member in which the first mentioned electrolyte and electrode are provided. The mounting means for the porous member includes an attaching means for attaching the porous member to the tube for movement therewith. In this embodiment, the sealing means permits relative rotation between the tube and the cylindrical member.

The preferred embodiment of the present invention preferably further includes an annular shoulder on the upper sealing means of the tube and a reduced portion above the shoulder. The cylindrical member then includes a stop means which engages this shoulder. A cap is also provided to which the reduced end is attached and a spring means is located between the cap and the cylindrical member for normally urging the stop means of the cylindrical member into contact with the shoulder of the upper sealing means to prevent relative rotation thereof by frictional contact. However, when the cap is pushed towards the cylindrical member, the stop means separates from the shoulder and the tube is easily rotated relative to the cylindrical member to move a different portion of the ring adjacent the aperture.

In the preferred embodiment, the indicating means includes a flange attached to the lower sealing means below the cylindrical member. This flange is provided with indicia about a circumference thereof. This indicia is thus located adjacent a reference marker provided on the cylindrical member.

It is an advantage of the present invention that a porous member is provided for a measuring electrode which is selectively moveable adjacent an aperture to bring a new portion of the porous member in position to cover the aperture when the portion previously covering the aperture becomes clogged.

It is also an advantage of the present invention that an indicating means is provided to indicate how many portions are available to be used on the porous member, and how many of these portions have already been used.

It is a further advantage of the present invention that the only can a fresh porous member portion be provided to cover the aperture when desired, but the portion in question can be troubleshooted by moving a new portion in position to determine the response of the measuring electrode assembly which will be different if the previous porous member portion was clogged.

Other features and advantages of the present invention are stated in or apparent from a detailed description of a presently preferred embodiment of the present invention found hereinbelow.

DETAILED DESCRIPTION OF THE PREFERRED EMBODIMENT

Figure 1:
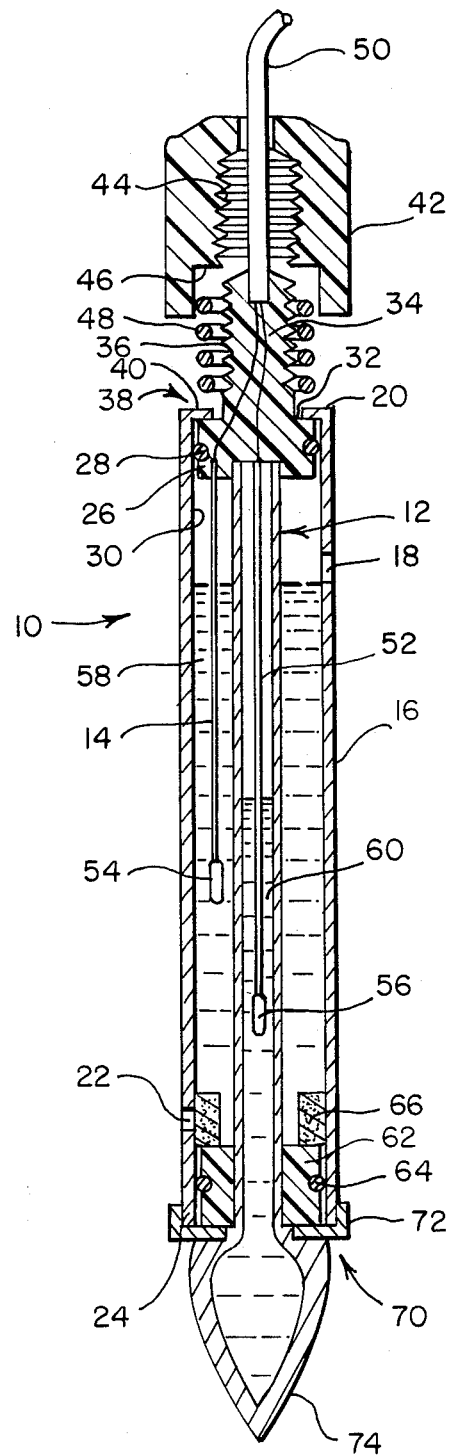
FIG. 1 is a cross-sectional elevation view of the electrode assembly according to the present invention.

With reference now to the drawings in which like numerals represent like elements throughout the two views, a measuring electrode assembly 10 is depicted in FIG. 1. Measuring electrode assembly 10 in this embodiment is a combination electrode assembly including a glass electrode member 12 and a reference electrode 14. Combination measuring electrode assembly 10 is typically used in making accurate pH measurements of solutions.

Measuring electrode assembly 10 includes an enclosed member in the form of a closed cylindrical member 16. Cylindrical member 16 has an aperture 18 adjacent an upper end 20 thereof and an aperture 22 adjacent a lower end 24 thereof. Adjacent upper end 20 of cylindrical member 16, an upper sealing means 26 is providd which closes off upper end 20 of cylindrical member 16. Upper sealing means 26 includes an O-ring 28 which contacts an inner wall 30 of cylindrical member 16. As shown, upper sealing means 26 also includes a shoulder 32 from which a reduced portion 34 extends upwards. Reduced portion 34 is provided with a series of threads 36. Upper end 20 of cylindrical member 16 includes a stop means 38 in the form of an inwardly directed flange 40 which engages shoulder 32 of upper sealing means 26 and stops cylindrical member 16 from passing off of upper sealing means 26.

Reduced portion 34 of upper sealing means 26 is attached to a cap 42 by the provision on cap 42 of threads 44 which mate with threads 36 of reduced portion 34. As shown, cap 42 includes an annular shoulder 46 adjacent threads 44 and reduced portion 34. Provided about reduced portion 34 is a spring means 48. When reduced portion 34 is received in cap 42, spring means 48 is compressed between annular shoulder 46 and flange 40 of cylindrical member 16.

Passing through cap 42 is a cable 50, typically a coax-type cable. Cable 50 includes two conductors which are respectively attached to reference electrode 14 and a glass electrode 52 which is disposed in glass electrode member 12. Reference electrode 14 and glass electrode 52 include respective tips 54 and 56 made of a silver-silver chloride material. Both tips 54 and 56 are maintained in a suitable respective electrolyte 58 and 60, such as potassium chloride. Electrolyte 60 in glass electrode member 12 is conveniently inserted in the top of glass electrode member 12 before this top is frictionally received in upper sealing means 26. Electrolyte 58 in cylindrical member 16 is conveniently introduced therein through aperture 18.

Located adjacent lower end 24 of cylindrical member 16 is a lower sealing means 62. Lower sealing means 62 includes an O-ring 64 which contacts inner wall 30 of cylindrical member 16. Lower sealing means 62 is securely attached to glass electrode member 12 as well as being in sealing contact with glass electrode member 12. Located above lower sealing means 62 is a porous plug member 66 which is typically made of glass frit. Porous plug member 66 is in the form of a ring having an outer diameter substantially the same as the diameter of inner wall 30 of cylindrical member 16. Thus, porous member 66 is snugly located adjacent inner wall 30 and, as shown, is positioned to cover aperture 22 in cylindrical member 16. Porous plug member 66 is also securely attached to lower sealing means 62 such that porous plug member 66 also moves as a unit with lower sealing means 62 and glass electrode member 12.

Provided adjacent lower end 24 of cylindrical member 16 is an indicating means 70. Indicating means 70 includes a flange 72 located about a bulbous tip 74 of glass electrode member 12. Flange 72 is securely attached to glass electrode member 12, as by attachment of flange 72 to lower sealing means 62. Flange 72 is preferably circular shaped and includes indicia 76 about the circumference of flange 72. Adjacent indicia 76 but on cylindrical member 16 is a reference marker 78. For convenience. reference marker 78 is located immediately below aperture 22.

In operation, measuring electrode assembly 10 functions in the following manner. Initially, measuring electrode assembly 10 is suitably preassembled as depicted in FIG. 1. In FIG. 1, glass electrode member 12 is shown with an electrolyte 60 and glass electrode 52 having tip 56 therein. It should be appreciated that electrolyte 60 is initially poured into glass electrode member 12 through an open top of glass electrode member 12 before glass electrode member 12 is frictionally received in upper sealing means 26. Upper sealing means 26 also seats glass electrode 52 so that glass electrode 52 is inserted in glass electrode member 12 as glass electrode member 12 is moved relative to glass electrode 52 and inserted in upper sealing means 26. It should also be appreciated that glass electrode member 12 is initially provided with flange 72, lower sealing means 62, and porous plug member 66 in place thereon. Conveniently, this is accomplished by attaching flange 72 and porous plug member 66 securely to lower sealing means 62. Lower sealing means 62 is then attached to glass electrode member 12 with a tight frictional fit or other suitable attaching means.

Once glass electrode member 12 is securely inserted in upper sealing means 26, upper sealing means 26 and glass electrode member 12 are inserted upwards through cylindrical member 16 to the position depicted in FIG. 1. In this position, flange 40 of cylindrical member 16 rests on shoulder 32 of upper sealing means 26. Also, lower sealing means 62 seals the bottom of cylindrical member 16 and porous plug member 66 is positioned adjacent aperture 22 to similarly seal aperture 22. It should be appreciated that reference electrode 14 is also seated in upper sealing means 26 so that reference electrode 14 is positioned in cylindrical member 16 as upper sealing means 26 and glass electrode member 12 are inserted in cylindrical member 16.

At a suitable junction of cable 50, spring means 48 and cap 42 are placed around cable 50 and moved to a position adjacent upper sealing means 26 as depicted in FIG. 1. From this position, reduced portion 34 of upper sealing means 26 is then threadably received in cap 22 by rotation of tip 74 of glass electrode member 12. When the top of reduced portion 34 seats in cap 42, spring means 48 pushes against annular shoulder 46 of cap 42 and against flange 40 of cylindrical member 12. Thus, flange 40 is resiliently pressed into frictional engagement with shoulder 32 of upper sealing means 26. Finally, at some time before use, electrolyte 58 is inserted in cylindrical member 16 through aperture 18 so that measuring electrode 10 is ready for use.

Figure 2:
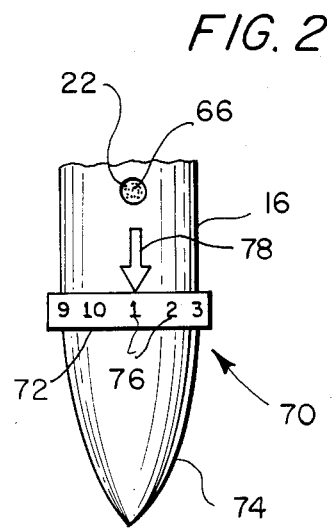
FIG. 2 is an elevation view of the lower portion of the electrode assembly depicted in FIG. 1.

When first used, indicating means 70 is preferably set so that indicia 76 indicating the number one is immediately adjacent reference marker 78 as depicted in FIG. 2. This is accomplished by pressing downwards on cap 42 at the same time that cylindrical member 16 is pushed upwards to compress spring means 48. As soon as a slight separation is achieved between flange 40 of cylindrical member 16 and shoulder 32 of upper sealing means 26, cylindrical member 16 is suitably rotated to position reference marker 18 adjacent the indicia for numeral one. In this position, the pressing force between cylindrical member 16 and cap 42 is stopped so that spring means 48 again presses flange 40 into frictional contact with shoulder 32. In this position, aperture 22 of cylindrical member 16 is thus covered by a corresponding "first" portion of porous plug member 66.

As measuring electrode assembly 10 is repeatedly used, the first portion of porous plug member 66 eventually becomes clogged. When the operator determines this, cylindrical member 16 is then rotated as explained above to bring reference marker 78 adjacent the indicia for numeral two. By doing this, aperture 22 of cylindrical member 16 is moved to a new "second" portion of porous plug member 66 which is not clogged so that measuring electrode assembly 10 continues to function as desired. This procedure of moving aperture 22 of cylindrical member 16 to a new portion of porous plug member 66 whenever the previous portion becomes clogged is thus repeated as often as necessary until all portions of porous plug member 66 have been used up. As illustrated in FIG. 2, indicia 76 indicates that 10 portions of porous plug member 66 are available for use.

When all of the portions of porous plug member 66 have been used, measuring electrode assembly 10 is simply disassembled by pulling glass electrode assembly 12 from upper sealing means 26. A new glass electrode member 12 can then be inserted in upper sealing means 26. Alternately, a new lower sealing means 62 with a new porous plug member 66 can be fitted on glass electrode member 12 after removal of the old upper sealing means 26. As a further alternative, lower sealing means 62 can be removed and subject to boiling in fresh potassium chloride solution. This will redissolve the precipitated silver chloride on porous plug member 66 without fear of damaging glass electrode member 12.

It should be appreciated that with measuring electrode assembly 10, it is easy to determine whether or not a portion of porous plug member 66 which has been used in test solutions has become plugged. This is simply done by measuring a test solution with measuring electrode assembly 10 and determining an output reading from this measurement. A new portion of porous plug member 66 is then easily and quickly moved into position to cover aperture 22 and the same test solution is again measured. If there is no difference in the reading of measuring electrode assembly between the two measurements, then the original portion of porous plug member 66 was not clogged and was functioning properly. However, where a discrepancy occurs between the two measurements, the original portion of porous plug member 66 was obviously clogged so that a new portion of porous plug member 66 should be left in position adjacent aperture 22 for further measurements.

It should also be appreciated that the changing of electrolyte 58 in cylindrical member 16 is also facilitated by the disclosed construction of measuring electrode assembly 10. Such a changing of electrolyte 58 is easily accomplished by pushing cylindrical member 16 against spring means 48 a sufficient distance so that porous plug member 66 no longer covers aperture 22. When this occurs, electrolyte 58 quickly drains out of aperture 22 as air is drawn in aperture 18. After drainage is complete, cylindrical member 16 is returned to the position where porous plug member 66 covers aperture 22 and new electrolyte 58 is introduced into cylindrical member 16 through aperture 18.

Although the present invention has been described with respect to an exemplary embodiment thereof, it will be understood by those of ordinary skill in the art that variations and modifications can be effected within the scope and spirit of the invention.

I claim:

1. A measuring electrode assembly for immersion in a solution comprising:
    an enclosed member having an aperture therein;
    an electrolyte in said enclosed member which is above the level of said aperture;
    an electrode in said enclosed member which is immersed in said electrolyte;
    a porous plug member through which ions are passed; and
    a mounting means for movably mounting said porous member such that one of a plurality of portions of said porous member covers said aperture and such that a plurality of portions of said porous member are selectively moveable to cover said aperture.

2. An electrode assembly as claimed in claim 1 wherein said enclosed member is cylindrically shaped and said aperture is provided in a cylindrical wall thereof; and wherein said porous member is in the shape of a ring.

3. An electrode assembly as claimed in claim 2 wherein said mounting means mounts said ring inside said cylindrical wall of said enclosed member.

4. An electrode assembly as claimed in claim 3 wherein said porous member is glass frit, wherein said electrode is silver-silver chloride, and wherein said electrolyte is potassium chloride.

5. An electrode assembly as claimed in claim 1 and further including an indicating means for indicating which one of the plurality of portions of said porous member is covering said aperture.

6. An electrode assembly as claimed in claim 5 wherein said indicating means includes an indicia member having indicia thereon which said indicia member is moved together with said porous member, and a reference marker on said enclosed member adjacent said indicia member.

7. A measuring electrode assembly for immersion in a solution comprising:
    a closed cylindrical member having an aperture at a lower end thereof;
    an electrolyte located in said cylindrical member above the level of said aperture;
    an electrode located in said electrolyte;
    a ring formed of an ion porous material and having an outer surface; and a mounting means for rotatably mounting said ring in said cylindrical member such that a portion of said outer surface of said ring is rotatable relative to and is covering said aperture in said cylindrical member.

8. An electrode assembly as claimed in claim 7 and further including an indicating means for indicating which one of a plurality of portions of said outer surface of said ring is covering said aperture.

9. An electrode assembly as claimed in claim 7 and further including:
   a glass electrode member having (a) a tube which is closed at both ends, (b) a second electrolyte in said tube, and (c) a second electrode located in said second electrolyte, said tube being disposed concentrially in and in spaced relationship to said cylindrical member; and
   upper and lower sealing means located about said tube at an upper end and a lower end thereof for sealing an annular space between said tube and said cylindrical member in which space said first mentioned electrolyte and electrode are provided.

10. An electrode assembly as claimed in claim 9 wherein said mounting means includes an attaching means for attaching said porous member to said tube for movement therewith, and wherein said sealing means permits relative rotation between said tube and said cylindrical member.

11. An electrode assembly as claimed in claim 10 wherein said upper sealing means of said tube includes an annular shoulder and a reduced portion, and wherein said cylindrical member includes a stop means for engaging said shoulder; and
   further including a cap to which said reduced portion is attached, and a spring means located between said cap and said cylindrical member for normally urging said stop means of said cylindrical member into frictional contact with said shoulder of said upper sealing means to prevent relative rotation thereof and such that when said cap is pushed towards said cylindrical member said stop means separates from said shoulder and said tube is easily rotated relative to said cylindrical member to move a different portion of said ring adjacent said aperture.

12. An electrode assembly as claimed in claim 11 further including an indicating means for indicating which one of a plurality of portions of said outer surface of said ring is covering said aperture.

13. An electrode assembly as claimed in claim 12 wherein said indicating means includes a flange attached to said lower sealing means below said cylindrical member, said flange having indicia about a circumference thereof.

14. An electrode assembly as claimed in claim 13 and further including a reference marker on said cylindrical member adjacent said flange.

15. An electrode assembly as claimed in claim 10 wherein said sealing means includes an O-ring disposed adjacent said cylindrical member.

* * * * *